United States Patent
Fujii et al.

(10) Patent No.: US 11,105,789 B2
(45) Date of Patent: *Aug. 31, 2021

(54) METHOD FOR EVALUATING CELLULOSE NANOFIBER DISPERSION, CELLULOSE NANOFIBER AQUEOUS DISPERSION, AND CELLULOSE NANOFIBER-CONTAINING FOOD, COSMETIC, AND RUBBER COMPOSITION

(71) Applicant: NIPPON PAPER INDUSTRIES CO., LTD., Tokyo (JP)

(72) Inventors: Takeshi Fujii, Tokyo (JP); Fumiko Iwahori, Tokyo (JP); Kaori Yamabe, Tokyo (JP); Takeshi Nakatani, Tokyo (JP); Shinji Sato, Tokyo (JP); Koji Kimura, Tokyo (JP)

(73) Assignee: NIPPON PAPER INDUSTRIES CO., LTD., Tokyo (JP)

( * ) Notice: Subject to any disclaimer, the term of this patent is extended or adjusted under 35 U.S.C. 154(b) by 395 days.

This patent is subject to a terminal disclaimer.

(21) Appl. No.: 16/310,952

(22) PCT Filed: Aug. 8, 2017

(86) PCT No.: PCT/JP2017/028736
§ 371 (c)(1),
(2) Date: Dec. 18, 2018

(87) PCT Pub. No.: WO2018/030392
PCT Pub. Date: Feb. 15, 2018

(65) Prior Publication Data
US 2019/0353634 A1 Nov. 21, 2019

(30) Foreign Application Priority Data

Aug. 8, 2016 (JP) .............................. JP2016-155387
Aug. 16, 2016 (JP) .............................. JP2016-159517
Sep. 29, 2016 (JP) .............................. JP2016-190681

(51) Int. Cl.
*G01N 33/34* (2006.01)
*C08L 1/02* (2006.01)
(Continued)

(52) U.S. Cl.
CPC .............. *G01N 33/343* (2013.01); *C08L 1/02* (2013.01); *G01N 1/2813* (2013.01); *G01N 1/38* (2013.01);
(Continued)

(58) Field of Classification Search
CPC ...... G01N 33/343; G01N 33/36; G01N 15/06; G01N 1/2813; G01N 1/38; G01N 31/22;
(Continued)

(56) References Cited

U.S. PATENT DOCUMENTS 5,644,003 A 7/1997 Arai et al.
9,863,920 B2 * 1/2018 Gaynor .................. G01N 21/73
(Continued)

FOREIGN PATENT DOCUMENTS

JP H06-234946 A 8/1994
JP H07-188597 A 7/1995
(Continued)

OTHER PUBLICATIONS

Sep. 19, 2019 Office Action issued in Korean Patent Application No. 10-2018-7035652.
(Continued)

*Primary Examiner* — Sang H Nguyen
(74) *Attorney, Agent, or Firm* — Oliff PLC (57) ABSTRACT

Provided is method for evaluating a cellulose nanofiber (CNF) dispersion, the method including: (1) a step of preparing 1.0 mass % of a CNF aqueous dispersion; (2) a step of adding a coloring material into the CNF aqueous
(Continued)

solution and stirring with a vortex mixer; (3) a step of sandwiching a film of the coloring material-containing CNF aqueous dispersion between two glass plates such that said film has a thickness of 0.15 mm; (4) a step of observing, with a microscope, the film of the coloring material-containing CNF aqueous dispersion sandwiched between the two glass plates; (5) a step of sorting observed aggregates by size (diameter along major axis) thereof; and (6) a step of calculating a CNF dispersion index from the number of sorted aggregates and evaluating the dispersibility of the CNF aqueous dispersion.

7 Claims, 4 Drawing Sheets

(51) Int. Cl.
| | |
|---|---|
| G01N 1/38 | (2006.01) |
| G01N 31/22 | (2006.01) |
| G01N 1/28 | (2006.01) |
| G01N 15/06 | (2006.01) |
| B82Y 30/00 | (2011.01) |
| B82Y 35/00 | (2011.01) |
| B82Y 40/00 | (2011.01) |

(52) U.S. Cl.
CPC .............. *G01N 15/06* (2013.01); *G01N 31/22* (2013.01); *B82Y 30/00* (2013.01); *B82Y 35/00* (2013.01); *B82Y 40/00* (2013.01)

(58) Field of Classification Search
CPC ........... G01N 21/84; G01N 2021/8444; A61K 8/731; A61K 8/027; A61K 8/044; A61K 2800/412; A61K 2800/10; C08L 1/04; C08L 1/02; C08L 21/00; A23L 33/24; A23L 5/00; A61Q 19/00; A21D 2/36; B82Y 30/00; B82Y 35/00; B82Y 40/00
See application file for complete search history.

(56) References Cited

U.S. PATENT DOCUMENTS

| | | | | |
|---|---|---|---|---|
| 2006/0019409 | A1* | 1/2006 | Nelson | G06K 9/00127 |
| | | | | 436/524 |
| 2008/0107789 | A1 | 5/2008 | Akimato | |
| 2010/0254961 | A1* | 10/2010 | Nishio | A61K 8/64 |
| | | | | 424/94.1 |
| 2014/0322327 | A1* | 10/2014 | Laukkanen | A61K 9/5042 |
| | | | | 424/488 |
| 2016/0319232 | A1* | 11/2016 | Noritomi | G01N 27/49 |
| 2018/0045706 | A1 | 2/2018 | Nakatani et al. | |
| 2019/0116858 | A1* | 4/2019 | Kawasaki | A23L 29/262 |

FOREIGN PATENT DOCUMENTS

| | | | |
|---|---|---|---|
| JP | H08-134329 | A | 5/1996 |
| JP | 2008-001728 | A | 1/2008 |
| JP | 2008-092914 | A | 4/2008 |
| JP | 2008-118988 | A | 5/2008 |
| JP | 2013-181167 | A | 9/2013 |
| JP | 2014-092551 | A | 5/2014 |
| JP | 2014-141658 | A | 8/2014 |
| JP | 2014-193959 | A | 10/2014 |
| JP | 2015-134873 | A | 7/2015 |
| JP | 2015-199966 | A | 11/2015 |
| WO | 2016/133076 | A1 | 8/2016 |

OTHER PUBLICATIONS

Aug. 28, 2020 Office Action issued in Chinese Patent Application No. 201780034935.1.
Sep. 12, 2017 International Search Report issued in International Patent Application No. PCT/JP2017/028736.
Apr. 1, 2020 Search Report issued in European Patent Application No. 17839462.3.
Mar. 31, 2020 Office Action issued in Korean Patent Application No. 2018-7035652.
Nov. 27, 2020 Office Action issued in Korean Patent Application No. 10-2018-7035652.
Feb. 12, 2019 International Preliminary Report on Patentability issued in International Patent Application No. PCT/JP2017/028736.
Apr. 22, 2021 Office Action issued in Korean Patent Application No. 10-2021-7002776.
May 7, 2021 Office Action issued in Chinese Patent Application No. 201780034935.3.
Jun. 18, 2021 Office Action issued in European Patent Application No. 17 839 462.3.
Jun. 29, 2021 Office Action issued in Japanese Patent Application No. 2018-533490.

* cited by examiner

METHOD FOR EVALUATING CELLULOSE NANOFIBER DISPERSION, CELLULOSE NANOFIBER AQUEOUS DISPERSION, AND CELLULOSE NANOFIBER-CONTAINING FOOD, COSMETIC, AND RUBBER COMPOSITION

TECHNICAL FIELD

The present invention relates to a method for evaluating a cellulose nanofiber dispersion, and the like.

BACKGROUND ART

Cellulose nanofibers (CNFs) are fine fibers having a fiber diameter in the order of about 4 to several hundred nanometers with high dispersibility in water-based media so that they are expected to be applied as reinforcing materials for resins; for maintaining the viscosity of foods, cosmetics, medical products or coatings and the like; for strengthening doughs as precursors of foodstuffs and holding water in them; for improving food stability; and as low-calorie additives or emulsion stabilizing aids (Patent Literature 1 and the like). When CNFs are used as additives, they are typically used in a dispersed state in water (i.e., in a wet state).

CITATION LIST

Patent Literature

Patent Literature 1: JP 2008-1728 A

SUMMARY OF INVENTION

Technical Problem

CNFs are expected to be applied for various purposes, but CNFs may associate with each other to form aggregates in CNF dispersions, thus inviting various problems. Therefore, it is necessary to ascertain whether or not aggregates exist in CNF dispersions in advance, and to remove or defibrate any aggregates in the CNF dispersions as necessary. However, CNFs are very thin fibers so that their dispersions are highly transparent. This caused the problem that aggregates of CNFs could not be visually identified if they existed.

In view of such circumstances, it is an object of the present invention to provide a method for quantitatively evaluating aggregates of CNFs in a CNF dispersion that cannot be visually determined. It is also an object of the present invention to provide a cellulose nanofiber aqueous dispersion having a CNF dispersion index equal to or less than a predetermined value, the CNF dispersion index evaluated by the evaluation method, and a food, a cosmetic, and a rubber composition containing the cellulose nanofiber aqueous dispersion or a cellulose nanofiber derived from the aqueous dispersion.

Solution to Problem

The present invention provides the following <1> to <7>.

<1> A method for evaluating a cellulose nanofiber dispersion, the method including the steps of: (1) preparing a 1.0% by mass cellulose nanofiber aqueous dispersion; (2) adding a color material containing 5 to 20% by mass of a colored pigment having an average particle size of 0.03 µm or more and 1 µm or less to 1 g of the cellulose nanofiber aqueous dispersion prepared in the step (1), followed by stirring for 1 minute with the maximum rotation number of a vortex mixer set; (3) sandwiching the cellulose nanofiber aqueous dispersion containing the color material obtained in the step (2) between two glass plates so that a film thickness of the cellulose nanofiber aqueous dispersion is 0.15 mm; (4) observing a film of the cellulose nanofiber aqueous dispersion containing the color material sandwiched between the two glass plates obtained in the step (3) with a microscope (magnification: 100 times); (5) measuring major axes of aggregates existing in a range of 3 mm×2.3 mm in the step (4), and classifying the observed aggregates into an oversize aggregate having a major axis of 150 µm or more, a large size aggregate having a major axis of 100 µm or more and less than 150 µm, a middle size aggregate having a major axis of 50 µm or more and less than 100 µm, and a small size aggregate having a major axis of 20 µm or more and less than 50 µm; and (6) counting the number of the aggregates classified in the step (5), and calculating a CNF dispersion index according to the equation 1 to evaluate dispersibility of the cellulose nanofiber aqueous dispersion, the equation 1:

CNF dispersion index=(the number of oversize aggregates×512+the number of large size aggregates×64+the number of middle size aggregates×8+the number of small size aggregates×1)=2.

<2> A cellulose nanofiber aqueous dispersion having a CNF dispersion index of 8000 or less, the CNF dispersion index determined by the method according to <1>.

<3> A food including the cellulose nanofiber aqueous dispersion according to <2> or a cellulose nanofiber derived from the aqueous dispersion according to <2>.

<4> A dumpling including the cellulose nanofiber aqueous dispersion according to <2> or a cellulose nanofiber derived from the aqueous dispersion according to <2>.

<5> A water-containing chocolate including the cellulose nanofiber aqueous dispersion according to <2> or a cellulose nanofiber derived from the aqueous dispersion according to <2>.

<6> A cosmetic including the cellulose nanofiber aqueous dispersion according to <2> or a cellulose nanofiber derived from the aqueous dispersion according to <2>.

<7> A rubber composition including the cellulose nanofiber aqueous dispersion according to <2> or a cellulose nanofiber derived from the aqueous dispersion according to <2>.

ADVANTAGEOUS EFFECTS OF INVENTION

The present invention can provide a method for quantitatively evaluating aggregates of CNFs in a CNF dispersion that cannot be visually determined. The present invention can also provide a cellulose nanofiber aqueous dispersion having a CNF dispersion index equal to or less than a predetermined value, the CNF dispersion index evaluated by the evaluation method, and a food, a cosmetic, and a rubber composition containing the cellulose nanofiber aqueous dispersion or a cellulose nanofiber derived from the aqueous dispersion.

DESCRIPTION OF EMBODIMENTS

A method for evaluating a cellulose nanofiber (CNF) dispersion of the present invention, the method includes: (1) preparing a 1.0% by mass cellulose nanofiber aqueous dispersion; (2) adding a color material containing 5 to 20% by mass of a colored pigment having an average particle size of 0.03 μm or more and 1 μm or less to 1 g of the cellulose nanofiber aqueous dispersion prepared in the step (1), followed by stirring for 1 minute with the maximum rotation number of a vortex mixer set; (3) sandwiching the cellulose nanofiber aqueous dispersion containing the color material obtained in the step (2) between two glass plates so that a film thickness of the cellulose nanofiber aqueous dispersion is 0.15 mm; (4) observing a film of the cellulose nanofiber aqueous dispersion containing the color material sandwiched between the two glass plates obtained in the step (3) with a microscope (magnification: 100 times); (5) measuring major axes of aggregates existing in a range of 3 mm×2.3 mm in the step (4), and classifying the observed aggregates; and (6) evaluating dispersibility of the cellulose nanofiber aqueous dispersion based on the number of the aggregates classified in the step (5). The method can quantitatively evaluate the difference in the dispersibility of the cellulose nanofiber dispersion having high transparency which does not exhibit any difference by visual evaluation or an optical measuring device and the like.

In the present invention, the term "aggregates of cellulose nanofibers (CNFs)" refers to poorly defibrated fibers produced during the defibration process described later, CNF network structures produced in dispersions, or aggregates produced during the concentration or drying of CNFs and the like.

In the present invention, the range "A to B" includes its endpoint values, i.e., A and B. The expression "A or B" includes either one or both of A and B.

(Cellulose Nanofibers)

Cellulose nanofibers (CNFs) are fine fibers having a fiber diameter of about 4 to 500 nm and an aspect ratio of 100 or more, and can be obtained by defibrating cellulose fibers having undergone a chemical treatment such as cationization or anionization. Examples of the anionization treatment include carboxylation (oxidation), carboxymethylation, esterification, and functionalization.

(Cellulose Raw Materials)

Examples of cellulose raw materials for manufacturing a chemically modified cellulose include those derived from plant materials (e.g., wood, bamboo, hemp, jute, kenaf, farm wastes, cloth, pulp), animal materials (e.g., Ascidiacea), algae, products produced by microorganisms (e.g., acetic acid bacteria (Acetobacter)), and the like. Examples of pulps include softwood unbleached kraft pulp (NUKP), softwood bleached kraft pulp (NBKP), hardwood unbleached kraft pulp (LUKP), hardwood bleached kraft pulp (LBKP), softwood unbleached sulfite pulp (NUSP), softwood bleached sulfite pulp (NBSP), thermomechanical pulp (TMP), recycled pulp, and waste paper pulp. Any of these materials can be used, but cellulose fibers derived from plants or microorganisms are preferred, among which cellulose fibers derived from plants are more preferred.

(Carboxymethylation)

When a carboxymethylated cellulose is used as a chemically modified cellulose in the present invention, the carboxymethylated cellulose may be obtained by carboxymethylating any one of the cellulose raw materials listed above by a known method, or may be commercially available. In either case, the degree of substitution with carboxymethyl group per anhydrous glucose unit of the cellulose is preferably 0.01 to 0.50. An example of a method for manufacturing such a carboxymethylated cellulose is as follows. A cellulose is used as a starting material in a solvent consisting of water or a lower alcohol in an amount of 3 to 20 times the mass of the cellulose. Specifically, water, methanol, ethanol, N-propyl alcohol, isopropyl alcohol, N-butanol, isobutanol, tert-butanol and the like can be used alone or as a combination of two or more of them. When a mixed solvent of water and a lower alcohol is used, the proportion of the lower alcohol is 60 to 95% by mass. A mercerizing agent consisting of an alkali metal hydroxide such as sodium hydroxide or potassium hydroxide is used in an amount of 0.5 to 20 molar equivalents per anhydrous glucose residue of the starting material. The starting material, the solvent, and the mercerizing agent are mixed to perform a mercerization process at a reaction temperature of 0 to 70° C., preferably 10 to 60° C. for a reaction period of 15 minutes to 8 hours, preferably 30 minutes to 7 hours. Then, a carboxymethylating agent is added in an amount of 0.05 to 10.0 molar equivalents per glucose residue to perform an etherification reaction at a reaction temperature of 30 to 90° C., preferably 40 to 80° C. for a reaction period of 30 minutes to 10 hours, preferably 1 hour to 4 hours.

(Carboxylation)

When a carboxylated (oxidized) cellulose is used as a chemically modified cellulose in the present invention, the carboxylated cellulose (also referred to as "oxidized cellulose") can be obtained by carboxylating (oxidizing) any one of the cellulose raw materials by a known method. The carboxy group content is preferably, but not limited to, 0.6 to 2.0 mmol/g, more preferably 1.0 mmol/g to 2.0 mmol/g based on the bone dry mass of the anionically modified cellulose nanofibers.

An example of a carboxylation (oxidation) method includes oxidizing a cellulose raw material using an oxidizing agent in water in the presence of a compound selected from the group consisting of an N-oxyl compound, a bromide, an iodide and a mixture thereof. This oxidation reaction allows the primary hydroxyl group at the C6 position of the glucopyranose ring on the surface of the cellulose to be selectively oxidized to give cellulose fibers having an aldehyde group and a carboxy group (—COOH) or a carboxylate group (—COO—) on their surface. During the reaction, the concentration of the cellulose is not particularly limited, but preferably 5% by mass or less.

The term "N-oxyl compound" refers to a compound capable of generating nitroxyl radicals. Any N-oxyl compounds can be used so far as they promote the intended oxidation reaction. Examples thereof include 2,2,6,6-tetramethylpiperidin-1-oxy radical (TEMPO) and derivatives thereof (e.g., 4-hydroxy-TEMPO).

The amount of the N-oxyl compound used is not particularly limited so far as it is a catalytic amount enough to oxidize the cellulose used as a raw material. For example, it is preferably 0.01 to 10 mmol, more preferably 0.01 to 1 mmol, still more preferably 0.05 to 0.5 mmol per gram of bone dry cellulose. It is preferably about 0.1 to 4 mmol/L of the reaction system.

The term "bromide" refers to a compound containing bromine, examples of which include alkali metal bromides that can be ionized by dissociation in water. The term "iodide" refers to a compound containing iodine, examples of which include alkali metal iodides. The amount of the bromide or iodide used can be selected in a range that can promote the oxidation reaction. The total amount of the bromide and iodide is preferably, for example, 0.1 to 100 mmol, more preferably 0.1 to 10 mmol, still more preferably 0.5 to 5 mmol per gram of bone dry cellulose.

Any known oxidizing agents can be used, including, for example, halogens, hypohalous acids, halous acids, perhalogenic acids or salts thereof, halogen oxides, peroxides and the like. Among these, sodium hypochlorite is preferred because it is inexpensive and less environmentally harmful. The amount of the oxidizing agent used is preferably 0.5 to 500 mmol, more preferably 0.5 to 50 mmol, still more preferably 1 to 25 mmol, most preferably 3 to 10 mmol per gram of bone dry cellulose, for example. It is preferably 1 to 40 mol per mole of the N-oxyl compound.

During the oxidation process of the cellulose, the reaction efficiently proceeds even under relatively mild conditions. Thus, the reaction temperature is preferably 4 to 40° C., or may be room temperature around 15 to 30° C. As the reaction proceeds, the pH of the reaction solution is found to decrease because carboxy groups are generated in the cellulose. To cause the oxidation reaction to efficiently proceed, an alkaline solution such as an aqueous sodium hydroxide solution is preferably added to maintain the pH of the reaction solution in the order of 8 to 12, preferably 10 to 11. The reaction medium is preferably water because of easy handling, low likelihood of side reactions and the like.

The reaction period in the oxidation reaction can be appropriately set depending on the extent to which oxidation proceeds, typically in the order of 0.5 to 6 hours, for example, 0.5 to 4 hours.

The oxidation reaction may be performed in two stages. For example, the oxidized cellulose obtained by filtration after the end of a first stage reaction can be oxidized again under the same or different reaction conditions, whereby the reaction is not inhibited by the salt produced as a by-product during the first stage reaction and efficient oxidation can be achieved.

Another examples of a carboxylation (oxidation) method include a method contacting a cellulose raw material with an ozone-containing gas. This oxidation reaction allows hydroxyl groups at least at the 2- and 6-positions of the glucopyranose ring to be oxidized and cellulose chains to be cleaved. The ozone concentration in the ozone-containing gas is preferably 50 to 250 g/m$^3$, more preferably 50 to 220 g/m$^3$. The amount of ozone added to the cellulose raw material is preferably 0.1 to 30 parts by mass, more preferably 5 to 30 parts by mass per 100 parts by mass of the solids content of the cellulose raw material. The ozonation temperature is preferably 0 to 50° C., more preferably 20 to 50° C. The ozonation period is not particularly limited, but in the order of 1 to 360 minutes, preferably 30 to 360 minutes. If the ozonation conditions are within these ranges, the cellulose can be prevented from being excessively oxidized and cleaved, thereby improving the yield of the oxidized cellulose. The ozonation may be followed by a post-oxidation process using an oxidizing agent. Examples of the oxidizing agent used in the post-oxidation process include, but not particularly limited to, chlorine compounds such as chlorine dioxide and sodium chlorite; and oxygen, hydrogen peroxide, persulfuric acid, and peracetic acid. For example, the post-oxidation process can be performed by dissolving one of these oxidizing agents in water or a polar organic solvent such as an alcohol to prepare a solution of the oxidizing agent and immersing the cellulose raw material in the solution.

The carboxy group content of the oxidized cellulose can be adjusted by controlling the reaction conditions described above such as the amount of the oxidizing agent added and the reaction period.

(Cationization)

When a carboxylated (oxidized) cellulose is used as a chemically modified cellulose in the present invention, the cationically modified cellulose can be obtained by reacting any one of the cellulose raw materials with a cationizing agent such as glycidyltrimethylammonium chloride, 3-chloro-2-hydroxypropyltrialkylammonium halide or a halohydrin form thereof and an alkali metal hydroxide (sodium hydroxide, potassium hydroxide and the like) as a catalyst in the presence of water or an alcohol having 1 to 4 carbon atoms. In this process, the degree of substitution with cationic group per glucose unit of the resulting cationically modified cellulose can be adjusted by controlling the amount of the reactant cationizing agent added or the proportion of water and the alcohol if they are used as a mixed solvent.

The degree of substitution with cationic group of the cationically modified cellulose is preferably 0.02 to 0.50 per glucose unit. When a cationic substituent is introduced into cellulose fibers, the cellulose fibers electrically repel each other. Therefore, the cellulose fibers into which a cationic substituent has been introduced can be readily defibrated into nanofibers. If the degree of substitution with cationic group is lower than 0.02 per glucose unit, they cannot be sufficiently defibrated into nanofibers. If the degree of substitution with cationic group is higher than 0.50 per glucose unit, however, they may be swollen or dissolved and may fail to form nanofibers. For efficient defibration, the oxidized cellulose raw material obtained as described above is preferably washed.

(Esterification)

An esterified cellulose can also be used as a cellulose. Examples of esterification include a method mixing a cellulose raw material with a powder or an aqueous solution of phosphate-based compound A, and a method adding an aqueous solution of phosphate-based compound A to a slurry of a cellulose raw material. Examples of the phosphate-based compound A include phosphoric acid, polyphosphoric acid, phosphorous acid, phosphoric acid, polyphosphonic acid or esters thereof. These may be in the form of a salt. Among these examples, phosphate group-containing compounds are preferred because they are inexpensive and easy to handle and the defibration efficiency can be improved by introducing a phosphate group into cellulose pulp fibers. Examples of the phosphate group-containing compounds include phosphoric acid, sodium dihydrogen phosphate, disodium hydrogen phosphate, trisodium phosphate, sodium pyrophosphate, sodium metaphosphate, potassium dihydrogen phosphate, dipotassium hydrogen phosphate, tripotassium phosphate, potassium pyrophosphate, potassium metaphosphate, ammonium dihydrogen phosphate, diammonium hydrogen phosphate, triammonium phosphate, ammonium pyrophosphate, and ammonium metaphosphate. These can be used alone or as a combination of two or more of them. Among them, phosphoric acid, sodium salts of phosphoric acid, potassium salts of phosphoric acid, and ammonium salts of phosphoric acid are preferred, and sodium dihydrogen phosphate and disodium hydrogen phosphate are more preferred from viewpoints that phosphate groups are efficiently introduced, defibration is promoted in the defibration process described later and they are readily industrially applied. The phosphate-based compound A is desirably used as an aqueous solution because the reaction can uniformly proceed and phosphate groups are more efficiently introduced. The pH of the aqueous solution of the phosphate-based compound A is preferably 7 or less to more efficiently introduce phosphate groups, whereas the pH is preferably 3 to 7 to reduce the hydrolysis of pulp fibers.

An example of a method for manufacturing a cellulose phosphate ester is as follows: To a suspension of a cellulose raw material having a solid content of 0.1 to 10% by weight is added phosphate-based compound A with stirring to introduce a phosphate group into the cellulose. The amount of the phosphate-based compound A added is preferably 0.2 to 500 parts by weight, more preferably 1 to 400 parts by weight expressed as the amount of elemental phosphorus per 100 parts by weight of the cellulose raw material. If the proportion of the phosphate-based compound A is equal to or higher than the lower limit indicated above, the yield of microfibrous cellulose can be further improved. However, it is not preferable in terms of costs to exceed the upper limit indicated above because the yield cannot be further improved.

In addition to the phosphate-based compound A, a powder or an aqueous solution of compound B may be mixed. The compound B is not particularly limited, but preferably a basic nitrogen-containing compound. The term "basic" as used here is defined to mean that aqueous solution turns pink-red in the presence of the phenolphthalein indicator or the aqueous solution has a pH of more than 7. The basic nitrogen-containing compound used in the present invention is not limited so far as the advantages of the present invention are achieved, but it is preferably an amino-containing compound. Examples of such compounds include urea, methylamine, ethylamine, trimethylamine, triethylamine, monoethanolamine, diethanolamine, triethanolamine, pyridine, ethylene diamine, and hexamethylene diamine. Among these, urea is preferred because it is inexpensive and excellent in handling. The amount of the compound B added is preferably 2 to 1000 parts by weight, more preferably 100 to 700 parts by weight per 100 parts by weight of the solids content of the cellulose raw material. The reaction temperature is preferably 0 to 95° C., more preferably 30 to 90° C. The reaction period is not particularly limited, but about 1 to 600 minutes, more preferably 30 to 480 minutes. If the esterification reaction conditions are within these ranges, the cellulose can be prevented from being excessively esterified and readily dissolved, thereby improving the yield of the cellulose phosphate ester. After the resulting cellulose phosphate ester suspension is dehydrated, it is preferably heated at 100 to 170° C. to reduce the hydrolysis of the cellulose. Further, it is heated at 130° C. or less, preferably 110° C. or less while water is contained during the heat treatment, and after water has been removed, it is preferably heated at 100 to 170° C.

Preferably, the degree of substitution with phosphate group of the cellulose phosphate ester is 0.001 to 0.40 per glucose unit. When a phosphate substituent is introduced into cellulose fibers, the cellulose fibers electrically repel each other. Therefore, the cellulose fibers into which a phosphate group has been introduced can be readily defibrated into nanofibers. If the degree of substitution with phosphate group is lower than 0.001 per glucose unit, they cannot be sufficiently defibrated into nanofibers. If the degree of substitution with phosphate group is higher than 0.40 per glucose unit, however, they may be swollen or dissolved and may fail to form nanofibers. For efficient defibration, the cellulose raw material esterified by phosphate groups obtained as described above is preferably boiled and then washed with cold water.

(Color Materials)

The color materials used in the present invention contain an organic pigment having an average particle size of 0.03 or more and 1 µm or less and a solvent, and the content of the organic pigment is 5 to 20% by mass. The average particle size of the organic pigment is a value measured by a laser diffraction particle size distribution analyzer (e.g., Mastersizer 3000 or Zetasizer Nano ZS manufactured by Malvern). When the pigments are not spherical, the average value of the major axis lengths is taken as the average particle size. Examples of the color of the color material include, but not particularly limited to, white, black, blue, red, yellow, and green.

(Colored Pigments)

In the present invention, the term "colored pigment" refers to a pigment having a color such as white, black, blue, red, yellow, or green, and its shape is not particularly limited to, a plate-like shape, a spherical shape, and a flaky shape. Examples of the colored pigments include inorganic pigments and organic pigments. Examples of the inorganic pigments include carbon black, black iron oxide, black complex metal oxides, zinc chromate, lead chromate, red lead, zinc phosphate, vanadium phosphate, calcium phosphate, aluminum phosphomolybdate, calcium molybdate, aluminum tripolyphosphate, bismuth oxide, bismuth hydroxide, basic bismuth carbonate, bismuth nitrate, bismuth silicate, hydrotalcite, zinc dust, micaceous iron oxide, calcium carbonate, barium sulfate, alumina white, silica, diatomaceous earth, kaolin, talc, clay, mica, barium oxide, organic bentonite, white carbon, titanium oxide, zinc oxide, antimony oxide, lithopone, white lead, perylene black, molybdenum red, cadmium red, red iron oxide, cerium sulfide, chrome yellow, cadmium yellow, yellow iron oxide, yellow ochre, bismuth yellow, sienna, amber, green earth, Mars Violet, ultramarine blue, Prussian blue, basic lead sulfate, basic lead silicate, zinc sulfide, antimony trioxide, calcium complexes, phthalocyanine blue, phthalocyanine green, ochre, aluminum powder, copper powder, brass powder, stainless steel powder, titanium oxide-coated mica, iron oxide-coated mica, copper zinc oxide, silver particles, anatase titanium oxide, iron oxide-based calcined pigments, conductive metal powder, and microwave-absorbing ferrites. Examples of the organic pigments include Quinacridone Red, Polyazo Yellow, Anthraquinone Red, Anthraquinone Yellow, Polyazo Red, Azo Lake Yellow, Perylene, Phthalocyanine Blue, Phthalocyanine Green, Isoindolinone Yellow, Watching Red, Permanent Red, Para Red, Toluidine Maroon, Benzidine Yellow, Fast Sky Blue, and Brilliant Carmine 6B. These pigments can be used alone or as a combination of two or more of them.

(Pigment Dispersions)

The solvent used for the color material of the present invention is preferably a water-based solvent. Examples of the water-based solvent include water, methanol, ethanol, N-propyl alcohol, isopropyl alcohol, N-butanol, isobutanol, tertiary butanol, linear or branched pentanediol, aliphatic ketones (e.g., acetone, methyl ethyl ketone, diacetone alcohol, etc.), polyols (e.g., ethylene glycol, diethylene glycol, triethylene glycol, etc.), polyglycols having a molar mass of 200 to 2000 g/mol, propylene glycol, dipropylene glycol, tripropylene glycol, trimethylolpropane, glycerol, thiodiglycol, 2-pyrrolidone, N-methylpyrrolidone, N-ethylpyrrolidone, 1,3-dimethylimidazolidinone, dimethylacetamide, dimethylformamide, and combinations thereof.

In order to stabilize the dispersibility of the organic pigment in the color material, it is possible to add a dispersant. Examples of the dispersant include higher fatty acids, higher fatty acid amides, metallic soaps, glycerin esters, hydrotalcite, polyethylene waxes, polypropylene waxes, glue, gelatin and the like, alone or as a combination of two or more of them.

The content of the colored pigment in the colored pigment dispersion is not limited, but it is 5 to 20% by mass. If the amount of the colored pigment contained is low, the photographs taken through an optical microscope look pale, but if the amount of the colored pigment contained is high, aggregates of the colored pigment may be generated.

In the present invention, preferred colored pigments are those providing a high contrast and less transparent to light (i.e., highly absorptive to light) during observation with an optical microscope, among which black pigments are more preferred. They preferably resist secondary aggregation or aggregation due to interaction with CNFs during observation. For example, colored pigment dispersions that can be used include sumi ink, Bokuteki, and pigment inks for inkjet printers. Sumi is surface-treated carbon black coated with a water-based resin on the surface and shows high dispersibility and resists secondary aggregation when it is mixed with a binder resin so that it achieves sufficiently high blackness even in CNF dispersions at relatively low concentrations. Sumi inks and Bokuteki are water-based dispersions containing surface-treated carbon black and they are manufactured by, for example, coating the surface of amorphous furnace black manufactured by the furnace process involving incomplete combustion of a petroleum- or coal-derived oil in a high-temperature gas and the like with a water-based resin, adding a glycol-based anti-freezing agent and a preservative as necessary, mixing them and slurring the mixture. In the present invention, commercially available products (e.g., "Bokuteki" manufactured by Kuretake Co., Ltd. and the like) can be used. Surface-treated carbon black or water-based dispersions thereof can also be prepared according to known methods (e.g., JP 07-188597 A or JP 06-234946 A). Sumi inks, Bokuteki, and pigment inks for inkjet printers may be used alone or as a combination of two or more of them.

(Observation with Optical Microscope)

In the present invention, a cellulose nanofiber dispersion containing a color material in which an appropriate amount (about 2 drops) of the above color material is added to 1 g of a dispersion having a concentration of 1.0% by mass is sandwiched between two glass plates (e.g., a combination of a slide glass and a cover glass) such that the film thickness of the dispersion is 0.15 mm, and observed with an optical microscope (including a microscope). The optical microscope is not particularly limited, and general optical microscopes (including microscopes) can be used. The magnification at which the cellulose nanofiber dispersion containing the color material is observed with the optical microscope is 100 times.

In the present invention, the dispersibility is quantitatively evaluated by using the CNF dispersion index. The CNF dispersion index refers to an indicator of the dispersibility of CNFs as a modification of the NEP index (e.g., disclosed in JP 08-134329 A), which is an indicator of the dispersibility of fibers. Specifically, the CNF dispersion index is determined as follows:

In the above observation, the major axis of an aggregate existing in a range of 3 mm×2.3 mm is measured, and the observed aggregate is classified into an oversize aggregate having a major axis of 150 μm or more, a large size aggregate having a major axis of 100 μm or more and less than 150 μm, a middle size aggregate having a major axis of 50 μm or more and less than 100 μm, and a small size aggregate having a major axis of 20 μm or more and less than 50 μm. The number of the classified aggregates is counted, and a CNF dispersion index is calculated according to the following equation.

CNF dispersion index=(the number of oversize aggregates×512+the number of large size aggregates×64+the number of middle size aggregates×8+the number of small size aggregates×1)÷2.

The evaluation method of the present invention can be applied even if other components such as water-soluble polymers as exemplified below are contained in the cellulose nanofiber dispersion. Examples of the water-soluble polymers include cellulose derivatives (carboxymethyl cellulose, methyl cellulose, hydroxypropyl cellulose, ethyl cellulose), xanthan gum, xyloglucan, dextrin, dextran, carrageenan, locust bean gum, alginic acid, alginates, pullulan, starches, potato starch, arrowroot starch, positive starch, phosphorylated starch, corn starch, gum arabic, gellan gum, polydextrose, pectin, chitin, water-soluble chitin, chitosan, casein, albumin, soy protein hydrolysate, peptone, polyvinyl alcohol, polyacrylamide, sodium polyacrylate, polyvinylpyrrolidone, polyvinyl acetate, polyamino acids, polylactic acid, polymalic acid, polyglycerin, latex, rosin sizing agents, petroleum resin sizing agents, urea resins, melamine resins, epoxy resins, polyamide resins, polyamide-polyamine resins, polyethyleneimines, polyamines, plant gums, polyethylene oxide, hydrophilic crosslinked polymers, polyacrylates, starch-polyacrylate copolymers, tamarind gum, guar gum, colloidal silica, and mixtures of one or more of them.

When a dispersion containing cellulose nanofibers and other components such as water-soluble polymers is evaluated, the dispersion is measured so that the CNF solid content is 1% by mass.

CNF redispersions evaluated to have good dispersibility in dispersion media according to the present invention not only show high solubility in applications for foods, chemical products and the like but also contain little undispersed materials, thereby providing smooth touch and improving the mouth feel when they are added to foods and the like. Thus, transparency, light transmittance, reproducibility of viscosity and the like are improved if the CNFs are used in liquid products such as cosmetics, and on the other hand, transparency, light transmittance and the like are improved if they are used in chemical products such as optical films.

Foods according to the present invention contain the CNF dispersion or CNFs from the dispersion. Such foods include desserts and snacks such as flour-based baked foods (e.g., biscuits, crackers, etc.), Japanese rice crackers (senbei, arare, okaki, etc.), sweet buns (e.g., rusks, etc.), fried dough foods (karinto (traditional Japanese sweet), etc.), chocolates, pastries and desserts, candies and caramels, higashi (traditional Japanese dry confectionary), uchigashi (a type of higashi), mamegashi (traditional Japanese bean snacks), and yokan (a bar of gelled sweet bean paste); and manju (traditional Japanese steamed buns with sweet paste fillings), dumplings, breakfast cereals, snacks, breads, and dough products such as noodles. The foods according to the present invention are preferably obtained by adding CNFs and optional ingredients such as sugar, oils and fats, eggs, dairy products, leavening agents, salt, emulsifiers, flavorings and the like to a flour of a cereal such as wheat, corn, rye, oat, or rice to manufacture a dough, which is then subjected to kneading and baking steps or subjected to kneading, fermentation and baking steps to prepare a food or dumplings containing the flour as the primary ingredient such as biscuits, cookies, crackers, wafers, snacks, breakfast cereals, breads, as well as Japanese rice crackers such as senbei, okaki, arare and the like. It should be noted that baking also includes frying with oil.

Examples of a dumpling and a water-containing chocolate will be shown below.

<Dumpling>

The term "dumpling" as used in the present invention refers to foods obtained by molding one or two or more raw materials selected from rice raw material, arrowroot starch, potato starch, bracken powder, dogtooth violet starch, tapioca starch, wheat flour, wheat starch, lotus root starch, sweet potato starch, corn starch, millet flour, and processed starch (enzymatically, physically and/or chemically processed starch) together with water and the like by a known method.

Examples of the rice raw material include glutinous rice, powders (shiratamako, etc.) made from glutinous rice, non-glutinous rice, powders (joshinko etc.) made from non-glutinous rice, and powders (dumpling powders) made from non-glutinous rice and glutinous rice. These rice raw materials may be used singly or in combination of two or more.

The shape of the dumpling in the present invention is not particularly limited, and can be used for known products such as kibi-dango (millet dumpling), gyuuhi (sweet rice flour paste), kushi-dango (dumplings on a bamboo skewer), sakura-mochi (rice cake wrapped in a pickled cherry leaf), daifuku-mochi (soft rice cake with azuki bean jam), kusa-mochi (rice flour dumpling mixed with mugwort), chimaki (cake wrapped in bamboo leaf), uguisu-mochi (rice cake sprinkled with green soybean flour), kashiwa-mochi (rice cake wrapped in an oak leaf), raw yatsuhashi (Japanese traditional sweet) containing azuki bean jam, and nerikiri (shaped bean paste).

In the present invention, the dumpling contains the cellulose nanofibers, which provides suppressed aging of the starch in the dumpling and exhibits more excellent texture. The amount of the cellulose nanofibers added in the dumpling is set such that the bone dry mass of the cellulose nanofibers is 0.05% by mass or more and 1.0% by mass or less, preferably 0.1% by mass or more and 1.0% by mass or less, more preferably 0.3% by mass or more and 1.0% by mass or less based on the total bone dry of the dumpling (containing cellulose nanofibers). The amount of the cellulose nanofibers added is controlled to 0.05% by mass or more, which exhibits suppressed aging of the starch and excellent texture. On the other hand, the amount added is set to 1.0% by mass or less, which makes it possible to suppress an adverse effect caused by an increase in viscosity.

<Water-Containing Chocolates>

The chocolates in the present invention usually refer not only to a so-called chocolate prescribed on the law and containing only cocoa butter as fat and oil components but also to various kinds of chocolates using hard butter as a cocoa butter substitute oil used in place of cocoa butter. Therefore, a chocolate dough can be used, which is obtained by rolling and conching treatments according to the ordinary method by using not only known commercially available chocolates themselves such as sweet chocolate or milk chocolate but also one or two or more of cacao mass, cocoa powder, cocoa butter, and hard butter and the like. In the present invention, it is also possible to use white chocolates obtained by using cocoa butter or hard butter and a solid content such as sugar, whole milk powder or skim milk powder without using cocoa or cacao mass, and it is also possible to use color chocolates having various flavors and colors in combination with a flavor material such as coffee or fruit.

As hydrophilic components, water, liquid sugar, natural raw creams, as well as creams using various animal and vegetable fats and oils conventionally developed such as milk, concentrated milk or various fruits, fruit juice, natural honey, foreign liquor and the like can be exemplified, and one or two or more thereof can be used.

In the present invention, the amount of the cellulose nanofibers added to the water-containing chocolate is preferably set such that the bone dry mass of the cellulose nanofibers in the water-containing chocolate is preferably 0.08% by mass or more, more preferably 0.15% by mass or more based on the total bone dry mass (containing cellulose nanofibers) of the water-containing chocolate.

The content is 0.08% by mass or more, which exhibits ganache-like body feeling having no stickiness even at normal temperatures, excellent shape retentivity, and very good texture such as smooth meltability in the mouth without causing viscosity. The bone dry mass of the cellulose nanofibers is set to 1.0% by mass or less based on the total bone dry mass of the water-containing chocolate, which makes it possible to suppress an adverse effect caused by an increase in viscosity.

The water-containing chocolate containing CNF can be used for bread and confectionary. In the present invention, the term "bread and confectionary" means those manufactured by adding cereal flours such as wheat flour (containing starch and gluten), yeast, salt, and water as main raw materials, and saccharides, dairy products, egg products, and edible fats and oils as auxiliary raw materials, and subjecting the kneaded dough to fermenting, shaping, baking, steaming, and heating such as frying, and examples thereof include breads such as pullman, French breads such as table roll, baguette, and battal, rolls such as sweet roll and table roll, sweet buns such as croissant, Danish pastry, and yeast doughnut, flour-based baked foods such as cakes, cookies, rusks, scones, crackers, and shortbreads, those containing custard cream, flour paste and the like, sponge cake, cakes such as butter cake, and donuts and biscuits.

The CNF dispersion index of CNFs added to food is preferably 8000 or less, more preferably 2000 or less, still more preferably 1000 or less, yet still more preferably 500 or less, further preferably 100 or less.

In the present invention, the appearance of the cellulose nanofibers to be added to the foods, the cosmetics, the rubber compositions and the like is not particularly limited, and may be a dispersion of cellulose nanofibers or a dry solid of cellulose nanofibers, or a wet solid which is an intermediate state thereof. In the present invention, the dry solid of cellulose nanofibers means a dry solid obtained by dehydrating and drying a dispersion containing cellulose nanofibers such that the water amount thereof is 12% or less. As the dry solid of cellulose nanofibers, a dried dispersion of cellulose nanofibers or a dried mixed liquid of cellulose nanofibers and a water-soluble polymer can be exemplified.

Cosmetics according to the present invention contain the CNF dispersion or CNFs from the dispersion. Examples of the cosmetics include skin care products such as creams, milky lotions, lotions, and serums; personal cleansing products such as soaps, facial cleansers, shampoos, and rinses; hair care products such as hair tonics, and hairstyling products; makeup products such as foundations, eye liners, mascaras, and lipsticks; oral care products such as toothpastes; and bath products.

The CNF dispersion index of CNFs added to the cosmetics is preferably 8000 or less, more preferably 2000 or less, still more preferably 1000 or less, yet still more preferably 500 or less, further preferably 100 or less.

Rubber compositions according to the present invention contain the CNF dispersion or CNFs from the dispersion. The rubber components are typically based on organic polymers and have a high elastic limit and a low elastic modulus. The rubber components are mainly classified into natural rubbers and synthetic rubbers, and either may be used or both may be combined in the present invention. The natural rubbers may be natural rubbers in the narrow sense that have not been chemically modified, or may be chemically modified natural rubbers such as chlorinated natural rubbers, chlorosulfonated natural rubbers, epoxylated natural rubbers, hydrogenated natural rubbers, deproteinized natural rubbers and the like. Examples of the synthetic rubbers include diene rubbers such as butadiene rubbers (BR), styrene-butadiene copolymer rubbers (SBR), isoprene rubbers (IR), butyl rubbers (IIR), acrylonitrile-butadiene rubbers (NBR), chloroprene rubbers (CR), styrene-isoprene copolymer rubbers, styrene-isoprene-butadiene copolymer rubbers, isoprene-butadiene copolymer rubbers; and ethylene-propylene rubbers (EPM, EPDM), acrylic rubbers (ACM), epichlorohydrin rubbers (CO, ECO), fluorinated rubbers (FKM), silicone rubbers (Q), urethane rubbers (U), and chlorosulfonated polyethylene (CSM).

The CNF dispersion index of CNFs added to the rubber composition is preferably 8000 or less, more preferably 2000 or less, still more preferably 1000 or less, yet still more preferably 500 or less, further preferably 100 or less.

EXAMPLES

Next, the present invention will be described in more detail based on Examples, but the following Examples specifically illustrate preferred examples of the present invention, and the present invention is not limited by these Examples at all.

(Measurement Method of Carboxy Group Content)

The carboxylated cellulose was prepared into 60 mL of a 0.5% by mass slurry (aqueous dispersion) and adjusted to pH 2.5 by adding a 0.1M aqueous hydrochloric acid solution, and then a 0.05N aqueous sodium hydroxide solution was added dropwise while the electric conductivity was measured until the pH reached 11. The carboxy group content was calculated from the amount of sodium hydroxide (a) consumed during the neutralization stage of the weak acid characterized by a moderate change in electric conductivity using the equation below:

Carboxy group content [mmol/g carboxylated cellulose]=a [mL]×0.05/mass [g] of carboxylated cellulose.

(Measuring Method of Carboxymethyl Group Content)

1) Precisely weighed about 2.0 g of the carboxymethylated cellulose fiber (bone dry) was added into a 300-mL Erlenmeyer flask with a ground glass stopper. 2) To this was added 100 mL of a mixture of 100 mL of special grade concentrated nitric acid in 1000 mL of methanol, and the mixture was agitated for 3 hours to convert the carboxymethyl cellulose salt (CM cellulose) into a hydrogen-substituted CM cellulose. 3) Precisely weighed 1.5 to 2.0 g of the hydrogen-substituted CM cellulose (bone dry) was added into a 300-mL Erlenmeyer flask with a ground glass stopper. 4) The hydrogen-substituted CM cellulose was wetted with 15 mL of 80% methanol, and 100 mL of 0.1N NaOH was added, and the mixture was agitated at room temperature for 3 hours. 5) Using phenolphthalein as an indicator, the excess of NaOH was back-titrated with 0.1N $H_2SO_4$. 6) The degree of substitution with carboxymethyl group (DS) was calculated by the equation below:

$$A=[(100\times F'-(0.1N\ H_2SO_4)\ (mL)\times F)\times 0.1]/(\text{bone dry mass }(g)\text{ of hydrogen-substituted CM cellulose})$$

$$DS=0.162\times A/(1-0.058\times A)$$

A: the amount of 1N NaOH (mL) required for neutralizing 1 g of the hydrogen-substituted CM cellulose
F': the factor of 0.1N $H_2SO_4$
F: the factor of 0.1N NaOH.

(Measuring Methods of Average Fiber Diameter and Aspect Ratio)

The average fiber diameter and average fiber length of the CNFs were analyzed on randomly chosen 200 fibers using a field emission scanning electron microscope (FE-SEM). The aspect ratio was calculated by the equation below:

Aspect ratio=average fiber length/average fiber diameter.

First, the CNF dispersion index was obtained by changing the manufacturing method of the CNFs and the kind of the color material, and shown below.

<Manufacture of CNF Dispersion 1>

To 500 ml of an aqueous solution containing 39 mg of TEMPO (manufactured by Sigma Aldrich) and 514 mg of sodium bromide dissolved therein was added 5 g (bone dry) of an unbeaten softwood bleached kraft pulp (brightness 85%), and the mixture was stirred until the pulp was homogeneously dispersed. An aqueous sodium hypochlorite solution was added to the reaction system in an amount of 5.7 mmol/g to start an oxidation reaction. During the reaction, the pH in the system decreased, and therefore, a 3M aqueous sodium hydroxide solution was sequentially added to adjust the reaction system to pH 10. The reaction was terminated when sodium hypochlorite has been consumed and the pH in the system became constant. After the reaction, the mixture was filtered through a glass filter to separate the pulp, and the pulp was thoroughly washed with water to give an oxidized pulp (carboxylated cellulose). The pulp yield was 90%, the time required for the oxidation reaction was 90 minutes, and the carboxy group content was 1.67 mmol/g.

The oxidized pulp obtained in the process described above was adjusted to 1.0% (w/v) (=1.0% by mass) with water, and treated in a ultra-high pressure homogenizer (20° C., 150 MPa) for five cycles to give an anionically modified cellulose nanofiber dispersion (CNF dispersion 1). The resulting fibers had an average fiber diameter of 4 nm and an aspect ratio of 150.

<Manufacture of CNF Dispersion 2>

A cellulose nanofiber dispersion (CNF dispersion 2) was prepared in the same manner as the CNF dispersion 1 except that the number of treatment cycles of the ultra-high pressure homogenizer was changed to one. The resulting fibers had an average fiber diameter of 20 nm and an aspect ratio of 250.

<Manufacture of CNF Dispersion 3>

In a stirrer capable of mixing pulp, 200 g of a pulp (NBKP (softwood bleached kraft pulp), manufactured by Nippon Paper Industries Co., Ltd.) on a dry mass basis and 111 g of sodium hydroxide on a dry mass basis were added and water was added in such an amount that the pulp had a solid content of 20% (w/v). Then, the mixture was stirred at 30° C. for 30 minutes, and then 216 g (on an active matter basis) of sodium monochloroacetate was added. The mixture was stirred for 30 minutes, and then warmed to 70° C. and stirred for 1 hour. Then, the reaction mixture was separated, neutralized, and washed to give a carboxymethylated pulp having a degree of substitution with carboxymethyl group of 0.25 per glucose unit. Then, the carboxymethylated pulp was adjusted to a solid content of 1% with water, and defibrated by 5 treatment cycles in a high pressure homogenizer at 20° C., 150 MPa to give a carboxymethylated cellulose fiber aqueous dispersion (CNF dispersion 3). The resulting fibers had an average fiber diameter of 15 nm and an aspect ratio of 150.

Example 1

Figure 1:
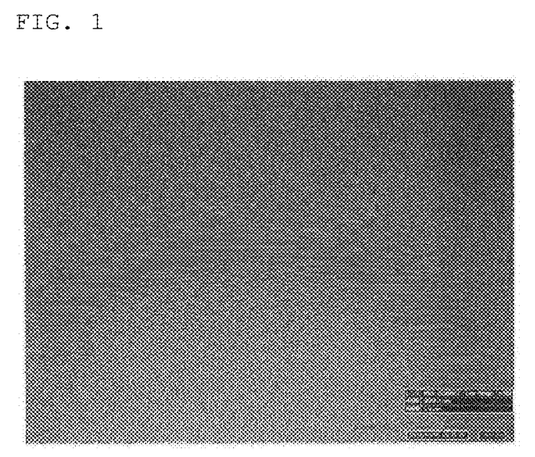
FIG. 1 shows the observation result of a CNF dispersion in Example 1 by an optical microscope.

To 1 g of the CNF dispersion 1 (a 1.0% by mass aqueous suspension of carboxylated CNFs) obtained as described above were added two drops of Bokuteki (having a solid content of 10% manufactured by Kuretake Co., Ltd.), and the suspension was stirred in a vortex mixer (equipment name: Automatic Lab-mixer HM-10H manufactured by IUCHI Corporation) for 1 minute with the maximum scale of the rotation number of the vortex mixer set. Next, the cellulose nanofiber dispersion containing Bokuteki was sandwiched between two glass plates so that the film thickness of the cellulose nanofiber dispersion was 0.15 mm, and observed with an optical microscope (digital microscope KH-8700 (manufactured by HIROX Co., Ltd.)) at a magnification of 100 times. The results are shown in FIG. 1. There was no aggregate in the observation range (2.3×3 mm), and the CNF dispersion index was 0. Using Zetasizer Nano ZS (manufactured by Malvern), the average particle size of the Bokuteki used was measured three times to be, on average, 0.22 µm.

Example 2

Figure 2:
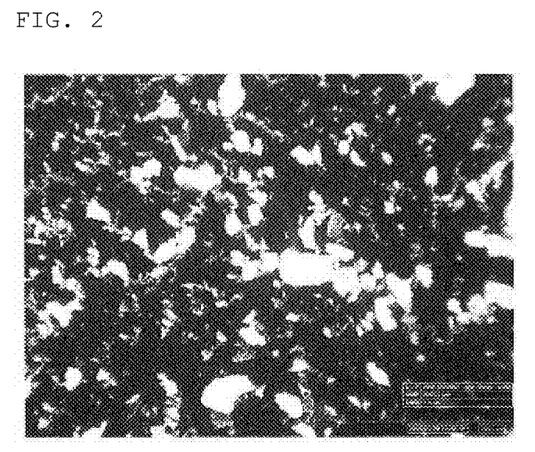
FIG. 2 shows the observation result of a CNF dispersion in Example 2 by an optical microscope.

The CNF dispersion 1 was dried in a forced air drying oven at 105° C., and water was added again to prepare an aqueous CNF dispersion (having a solid content of 1.0% by mass), which was stirred by using T.K. HOMO MIXER (6,000 rpm) for 60 minutes, to give a CNF dispersion. An experiment was conducted in the same manner as in Example 1 except that the CNF dispersion was used in place of the CNF dispersion 1, and the resulting dispersion was observed with an optical microscope. The results are shown in FIG. 2. The CNF dispersion index was 1825.

Example 3

Figure 3:
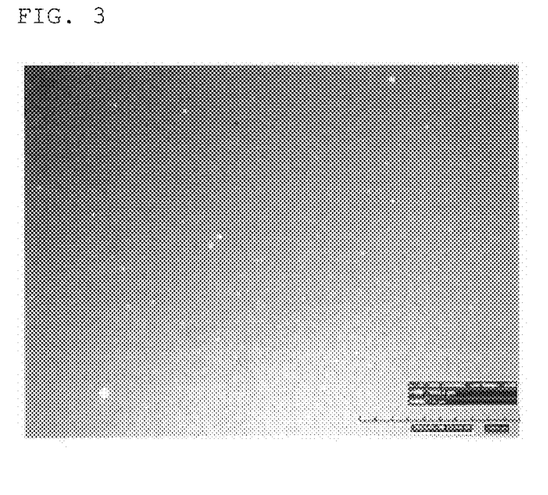
FIG. 3 shows the observation result of a CNF dispersion in Example 3 by an optical microscope.

A CMC-containing CNF dispersion prepared by adding a 1% by mass CMC aqueous solution to 100 parts by mass of the bone dry solid content of the CNF dispersion 1 for mixing so that the bone dry solid content of carboxymethyl cellulose (CMC) was 40 parts was dried in a forced air drying oven at 105° C., to give a dry solid containing CMC and CNF. Next, water was added to the dried solid so that the solid content of CNF was 1% by mass, and the mixture was stirred for 60 minutes using T.K. HOMO MIXER (6,000 rpm) to give a CMC-containing CNF dispersion. An experiment was conducted in the same manner as in Example 1 except that the CMC-containing CNF dispersion was used, and the resulting dispersion was observed with an optical microscope. The results are shown in FIG. 3. The CNF dispersion index was 24.

Example 4

Figure 4:
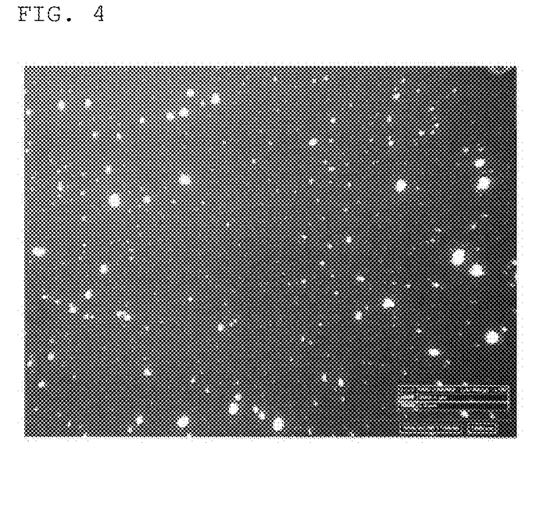
FIG. 4 shows the observation result of a CNF dispersion in Example 4 by an optical microscope.

Water was added to the dried solid used in Example 3 so that the solid content of CNF was 1% by mass, and the mixture was stirred for 60 minutes using T.K. HOMO MIXER (1,000 rpm) to give a CMC-containing CNF dispersion. An experiment was conducted in the same manner as in Example 1 except that the CMC-containing CNF dispersion was used in place of the CNF dispersion 1, and the resulting dispersion was observed with an optical microscope. The results are shown in FIG. 4. The CNF dispersion index was 252.

Example 5

Figure 5:
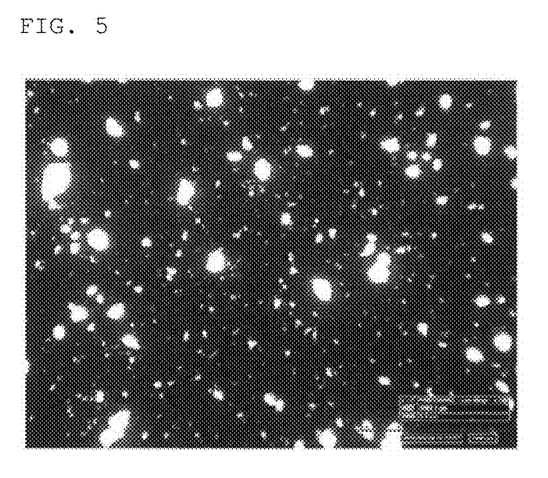
FIG. 5 shows the observation result of a CNF dispersion in Example 5 by an optical microscope.

Water was added to the dried solid used in Example 3 so that the solid content of CNF was 1% by mass, and the mixture was stirred for 180 minutes using T.K. HOMO MIXER (600 rpm) to give a CMC-containing CNF dispersion. An experiment was conducted in the same manner as in Example 1 except that the CMC-containing CNF dispersion was used in place of the CNF dispersion 1, and the resulting dispersion was observed with an optical microscope. The results are shown in FIG. 5. The CNF dispersion index was 942.

Example 6

A dispersion was observed with an optical microscope in the same manner as in Example 1 except that the Bokuteki used was changed from Bokuteki (manufactured by Kuretake Co., Ltd.) to Bokuteki (manufactured by KAIMEI & Co., Ltd.). As a result, it could be confirmed that no aggregates were contained in the CNF dispersion (the CNF dispersion index: 0). Using Zetasizer Nano ZS (manufactured by Malvern), the average particle size of the Bokuteki was measured three times to be, on average, 0.09 µm.

Example 7

An experiment was conducted in the same manner as in Example 1 except that the Bokuteki used was changed to Bokuteki obtained by grinding an inkstick (manufactured by Kuretake Co., Ltd.) against an inkstone with water, and the resulting dispersion was observed with an optical microscope. As a result, it could be confirmed that no aggregates were contained in the CNF dispersion (the CNF dispersion index: 0). Using Zetasizer Nano ZS (manufactured by Malvern), the average particle size of the Bokuteki was measured three times to be, on average, 0.51 µm.

Example 8

An experiment was conducted in the same manner as in Example 1 except that the Bokuteki used was changed to an "aqueous pigment ink" manufactured according to the manufacturing method described in "Example 1" of JP No. 2015-199966 A, and the resulting dispersion was observed with an optical microscope. As a result, it could be confirmed that no aggregates were contained in the CNF dispersion (the CNF dispersion index: 0).

Example 9

An experiment was conducted in the same manner as in Example 1 except that the CNF dispersion 2 (a 1.0% by mass aqueous suspension of carboxylated CNF) obtained as described above was used in place of the CNF dispersion 1, and the resulting dispersion was observed with an optical microscope. As a result, the CNF dispersion index was 3,500.

Example 10

An experiment was conducted in the same manner as in Example 1 except that the CNF dispersion 3 (a 1.0% by mass aqueous suspension of carboxymethylated CNF) obtained as described above was used in place of the CNF dispersion 1, and the resulting dispersion was observed with an optical microscope. As a result, it could be confirmed that no aggregates were contained in the CNF dispersion (the CNF dispersion index: 0).

Reference Example 1

Figure 6:
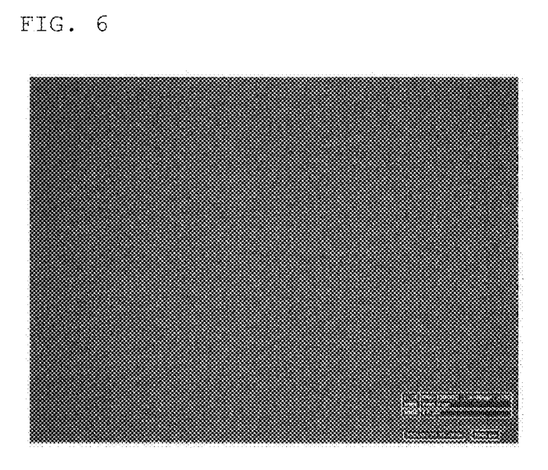
FIG. 6 shows the observation result of a CNF dispersion in Reference Example 1 by an optical microscope.

An experiment was conducted in the same manner as in Example 1 except that no Bokuteki was added dropwise to the CNF dispersion 1 used in Example 1, and the resulting dispersion was observed with an optical microscope. The results are shown in FIG. 6. The CNF dispersion index was 0.

Reference Example 2

Figure 7:
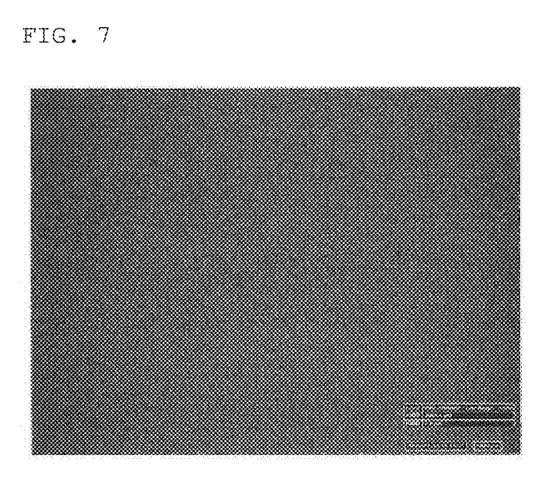
FIG. 7 shows the observation result of a CNF dispersion in Reference Example 2 by an optical microscope.

An experiment was conducted in the same manner as in Example 1 except that no Bokuteki was added dropwise to the CNF dispersion obtained through the drying and redispersing steps used in Example 2, and the resulting dispersion was observed with an optical microscope. The results are shown in FIG. 7. The CNF dispersion index was 0.
<Results>
It became clear that the CNF dispersion to which the color material such as Bokuteki is added is observed with the optical microscope, which makes it possible to easily determine the presence or absence of the aggregates in the CNF dispersion which has been hardly determined, and the dispersibility can be quantitatively evaluated by using the CNF dispersion index.

Next, Examples of a "dumpling" will be shown. In the following Examples, the CNF dispersion index was measured in the same manner as in Example 1.
<Manufacture of CNF Dispersion 4>
To 500 mL of an aqueous solution of 780 mg of TEMPO (manufactured by Sigma Aldrich) and 75.5 g of sodium bromide dissolved therein was added 500 g (bone dry) of an unbeaten softwood bleached kraft pulp (brightness 85%), and the mixture was stirred until the pulp was homogeneously dispersed. An aqueous sodium hypochlorite solution was added to the reaction system in an amount of 6.0 mmol/g to start an oxidation reaction. During the reaction, the pH in the system decreased, and therefore, a 3M aqueous sodium hydroxide solution was sequentially added to adjust the reaction system to pH 10. The reaction was terminated when sodium hypochlorite has been consumed and the pH in the system became constant. After the reaction, the mixture was filtered through a glass filter to separate the pulp, and the pulp was thoroughly washed with water to give an oxidized pulp (carboxylated cellulose). The pulp yield was 90%, the time required for the oxidation reaction was 90 minutes, and the carboxy group content was 1.6 mmol/g.

The oxidized pulp obtained in the process described above was adjusted to 1.0% (w/v) with water, and treated in a ultra-high pressure homogenizer (20° C., 150 MPa) for three cycles to give a cellulose nanofiber dispersion (CNF dispersion 4). The resulting fibers had an average fiber diameter of 3 nm and an aspect ratio of 250. The CNF dispersion index of the CNF dispersion 4 was 0.
<Manufacture of CNF Dispersion 5>
A cellulose nanofiber dispersion (CNF dispersion 5) was prepared in the same manner as the CNF dispersion 4 except that the number of treatment cycles of the ultra-high pressure homogenizer was changed to one. The resulting fibers had an average fiber diameter of 20 nm and an aspect ratio of 250. The CNF dispersion index of the CNF dispersion 5 was 3500.
<Manufacture of CNF Dispersion 6>
In a stirrer capable of mixing pulp, 200 g of a pulp (NBKP (softwood bleached kraft pulp), manufactured by Nippon Paper Industries Co., Ltd.) on a dry mass basis and 111 g of sodium hydroxide on a dry mass basis were added and water was added in such an amount that the pulp had a solid content of 20% (w/v). Then, the mixture was stirred at 30° C. for 30 minutes, and then 216 g (on an active matter basis) of sodium monochloroacetate was added. The mixture was stirred for 30 minutes, and then warmed to 70° C. and stirred for 1 hour. Then, the reaction mixture was separated, neutralized, and washed to give a carboxymethylated pulp having a degree of substitution with carboxymethyl group of 0.25 per glucose unit. Then, the carboxymethylated pulp was adjusted to a solid content of 1% with water, and defibrated by 5 treatment cycles in a high pressure homogenizer at 20° C., 150 MPa to give a carboxymethylated cellulose fiber aqueous dispersion (CNF dispersion 6). The resulting fibers had an average fiber diameter of 15 nm and an aspect ratio of 150. The CNF dispersion index of the CNF dispersion 6 was 0.

Example 11

A cellulose nanofiber dispersion (0.2% by mass, 400 g) obtained by diluting the CNF dispersion 4 with water was heated to 90° C. in a microwave oven, and added to 240 g of joshinko (rice flour) (manufactured by Hinomoto King Co., Ltd.). The mixture was sufficiently kneaded with a spatula. Thereafter, the resulting dough was broken and rolled so that the amount of the dough was 12 g on a dish on which a cooking sheet was laid, and heated in a microwave oven to manufacture dumplings. The bone dry mass of the additive cellulose nanofibers of the present invention in the dumplings was 0.33% by mass based on the joshinko. The resulting dumplings were tested for the degree of progression of aging of the starch and the ease of bite by the following method.
<Degree of Progression of Aging>
Ten panelists sampled the dumplings that had been allowed to stand for two days, and subjected the degree of hardness compared with that when sampling on the day of manufacture to sensory evaluation according to the following 5-point method. The average score thereof was taken as the evaluation score. The results are shown in Table 1.
Score 5: Difference enough to be ignored.
Score 3: Slightly hard feeling.
Score 1: A larger significant difference causes harder feeling.
<Texture>
Ten panelists sampled dumplings on the day of manufacture, and evaluated texture (ease of bite) according to the following 5-point method, and the average score thereof was taken as the evaluation score. The results are shown in Table 1.

Score 5: Easily bitten.
Score 3: Having slight mochi-like texture.
Score 1: Hardly bitten, and having strong mochi-like texture.

Example 12

A dumpling was manufactured and evaluated in the same manner as in Example 11 except that the CNF dispersion 4 was changed to the CNF dispersion 5.

Example 13

A dumpling was manufactured and evaluated in the same manner as in Example 11 except that the CNF dispersion 4 was changed to the CNF dispersion 6.

Comparative Example 1

A dumpling was manufactured and evaluated in the same manner as in Example 11 except that water was used in place of the cellulose nanofiber dispersion in Example 11.

Comparative Example 2

A dumpling was manufactured and evaluated in the same manner as in Example 11 except that a carboxymethylated cellulose dispersion (trade name: F350HC-4, manufactured by Nippon Paper Industries Co., Ltd.) was used in place of the cellulose nanofiber dispersion in Example 11.

pulp was thoroughly washed with water to give an oxidized pulp (carboxylated cellulose). The pulp yield was 90%, the time required for the oxidation reaction was 90 minutes, and the carboxy group content was 1.6 mmol/g.

The oxidized pulp obtained in the process described above was adjusted to 1.0% (w/v) with water, and treated in a ultra-high pressure homogenizer (20° C., 150 MPa) for three cycles to give a cellulose nanofiber dispersion (CNF dispersion 7). The resulting fibers had an average fiber diameter of 3 nm and an aspect ratio of 250. The CNF dispersion index of the CNF dispersion 7 was 0.

<Manufacture of CNF Dispersion 8>

In a stirrer capable of mixing pulp, 200 g of a pulp (NBKP (softwood bleached kraft pulp), manufactured by Nippon Paper Industries Co., Ltd.) on a dry mass basis and 111 g of sodium hydroxide on a dry mass basis were added and water was added in such an amount that the pulp had a solid content of 20% (w/v). Then, the mixture was stirred at 30° C. for 30 minutes, and then 216 g (on an active matter basis) of sodium monochloroacetate was added. The mixture was stirred for 30 minutes, and then warmed to 70° C. and stirred for 1 hour. Then, the reaction mixture was separated, neutralized, and washed to give a carboxymethylated pulp having a degree of substitution with carboxymethyl group of 0.25 per glucose unit. Then, the carboxymethylated pulp was adjusted to a solid content of 1% with water, and defibrated by 5 treatment cycles in a high pressure homogenizer at 20° C., 150 MPa to give a carboxymethylated cellulose fiber

TABLE 1

|  | Example 11 | Example 12 | Example 13 | Comparative Example 1 | Comparative Example 2 |
|---|---|---|---|---|---|
| Modification of CNF | Oxidization | Oxidization | CM | — | — |
| Degree of progression of aging | 4.2 | 4.6 | 4.6 | 1.2 | 2.8 |
| Texture | 4.8 | 3.6 | 4.2 | 2.4 | 3.0 |

As is apparent from the results of Table 1, Examples 11, 12, and 13 containing cellulose nanofibers were not aged as compared with Comparative Example 1 not containing cellulose nanofibers. It is found that, in Examples 11, 12, and 13 containing cellulose nanofibers, aging does not proceed as compared with Comparative Example 2 using carboxymethyl cellulose as microcrystalline cellulose, which provides good texture (ease of bite).

Next, Examples of "water-containing chocolate" will be shown. In the following Examples, the CNF dispersion index was measured in the same manner as in Example 1.

<Manufacture of CNF Dispersion 7>

To 500 mL of an aqueous solution of 780 mg of TEMPO (manufactured by Sigma Aldrich) and 75.5 g of sodium bromide dissolved therein was added 500 g (bone dry) of an unbeaten softwood bleached kraft pulp (brightness 85%), and the mixture was stirred until the pulp was homogeneously dispersed. An aqueous sodium hypochlorite solution was added to the reaction system in an amount of 6.0 mmol/g to start an oxidation reaction. During the reaction, the pH in the system decreased, and therefore, a 3M aqueous sodium hydroxide solution was sequentially added to adjust the reaction system to pH 10. The reaction was terminated when sodium hypochlorite has been consumed and the pH in the system became constant. After the reaction, the mixture was filtered through a glass filter to separate the pulp, and the aqueous dispersion (CNF dispersion 8). The resulting fibers had an average fiber diameter of 15 nm and an aspect ratio of 150. The CNF dispersion index of the CNF dispersion 8 was 0.

<Manufacture of CNF Dispersion 9>

200 g of a pulp (NBKP, manufactured by Nippon Paper Industries Co., Ltd.) on a dry mass basis and 24 g of sodium hydroxide on a dry mass basis were added to a pulper capable of stirring the pulp, and water was added so that a pulp solid concentration was 15%. Then, the mixture was stirred at 30° C. for 30 minutes, and then warmed to 70° C., 200 g (on an active matter basis) of 3-chloro-2-hydroxypropyltrimethylammonium chloride as a cationizing agent was added. After the reaction for 1 hour, the reaction mixture was separated, neutralized, and washed to give a cationically modified cellulose having a degree of substitution with cationic group of 0.05 per glucose unit. Then, the cationically modified pulp was adjusted to a solid concentration of 1%, and defibrated by 2 treatment cycles in a high pressure homogenizer at 20° C., 140 MPa to give a cellulose nanofiber dispersion (CNF dispersion 9). The resulting fibers had an average fiber diameter of 25 nm and an aspect ratio of 150. The CNF dispersion index of the CNF dispersion 9 was 0.

Example 14

The CNF dispersion 7 obtained above was dried in a drying oven at 105° C. to give a CNF dried solid having a water amount of 7%. The resulting CNF dried solid was pulverized by a dry mill to give additive cellulose nanofibers.

100 g of raw cream and the above additive cellulose nanofibers were mixed, and stirred until the granular mass of the cellulose nanofibers disappeared while being warmed. After stirring, 200 g of crumbled chocolate was added and melted. This dough was refrigerated and hardened to give a water-containing chocolate. The amount (bone dry mass) of the additive cellulose nanofibers added was 0.16% by mass based on the mass of the water-containing chocolate. The resulting water-containing chocolate was tested for shape retentivity, stickiness, and texture.

<Shape Retentivity/Stickiness>

The cooled water-containing chocolate was taken by hand, and subjected to sensory evaluation according to the following criteria. The results are shown in Table 2.
A: A chocolate hardly adheres to the hands, and keeps its shape for a long time even at normal temperatures.
B: A chocolate slightly adheres to the hands, and has its shape collapsing at normal temperatures after several hours.
C: A chocolate adheres to the hands in large quantity, and has its original shape collapsing soon.

<Texture>

Ten panelists sampled the chocolates, and evaluated texture (meltability in the mouth) according to the following 5-point method. The average score thereof was taken as the evaluation score. The results are shown in Table 2.
Score 5: Smooth and fresh meltability in the mouth.
Score 3: No viscosity and smooth meltability in the mouth.
Score 1: Viscosity and lack in smoothness.

Example 15

A water-containing chocolate was manufactured and tested in the same manner as in Example 14 except that the CNF dispersion 7 of Example 14 was changed to the CNF dispersion 8.

Comparative Example 3

A water-containing chocolate was manufactured and tested in the same manner as in Example 14 except that additive cellulose nanofibers were not used.

Comparative Example 4

A water-containing chocolate was manufactured and tested in the same manner as in Example 14 except that a carboxymethylated cellulose (trade name: F350HC-4, manufactured by Nippon Paper Industries Co., Ltd.) was used in place of the additive cellulose nanofibers.

TABLE 2

| | Example 14 | Example 15 | Comparative Example 3 | Comparative Example 4 |
|---|---|---|---|---|
| Shape retentivity, stickiness | A | A | C | B |
| Texture | 4.0 | 4.2 | 3.8 | 2.2 |

As is apparent from the results in Table 2, Example 14 and Example 15 containing cellulose nanofibers had better shape retentivity than that of Comparative Example 3 not containing cellulose nanofibers. It is found that Example 14 and Example 15 have better shape retentivity and meltability in the mouth than those of Comparative Example 4 using a carboxymethylated cellulose.

Next, Examples of "cosmetics" will be shown. In the following Examples, the CNF dispersion index was measured in the same manner as in Example 1.

<Manufacture of CNF Dispersion 10>

To 500 mL of an aqueous solution of 780 mg of TEMPO (manufactured by Sigma Aldrich) and 75.5 g of sodium bromide dissolved therein was added 500 g (bone dry) of an unbeaten softwood bleached kraft pulp (brightness 85%), and the mixture was stirred until the pulp was homogeneously dispersed. An aqueous sodium hypochlorite solution was added to the reaction system in an amount of 6.0 mmol/g to start an oxidation reaction. During the reaction, the pH in the system decreased, and therefore, a 3M aqueous sodium hydroxide solution was sequentially added to adjust the reaction system to pH 10. The reaction was terminated when sodium hypochlorite has been consumed and the pH in the system became constant. After the reaction, the mixture was filtered through a glass filter to separate the pulp, and the pulp was thoroughly washed with water to give an oxidized pulp (carboxylated cellulose). The pulp yield was 90%, the time required for the oxidation reaction was 90 minutes, and the carboxy group content was 1.6 mmol/g.

The oxidized pulp obtained in the process described above was adjusted to 1.0% (w/v) with water, and treated in a ultra-high pressure homogenizer (20° C., 150 MPa) for three cycles to give a cellulose nanofiber dispersion (CNF dispersion 10). The resulting fibers had an average fiber diameter of 3 nm and an aspect ratio of 250. The CNF dispersion index of the CNF dispersion 10 was 0.

<Manufacture of CNF Dispersion 11>

In a stirrer capable of mixing pulp, 200 g of a pulp (NBKP (softwood bleached kraft pulp), manufactured by Nippon Paper Industries Co., Ltd.) on a dry mass basis and 111 g of sodium hydroxide on a dry mass basis were added and water was added in such an amount that the pulp had a solid content of 20% (w/v). Then, the mixture was stirred at 30° C. for 30 minutes, and then 216 g (on an active matter basis) of sodium monochloroacetate was added. The mixture was stirred for 30 minutes, and then warmed to 70° C. and stirred for 1 hour. Then, the reaction mixture was separated, neutralized, and washed to give a carboxymethylated pulp having a degree of substitution with carboxymethyl group of 0.25 per glucose unit. Then, the carboxymethylated pulp was adjusted to a solid content of 1% with water, and defibrated by 5 treatment cycles in a high pressure homogenizer at 20° C., 150 MPa to give a carboxymethylated cellulose fiber aqueous dispersion (CNF dispersion 11). The resulting fibers had an average fiber diameter of 15 nm and an aspect ratio of 150. The CNF dispersion index of the CNF dispersion 11 was 0.

<Manufacture of CNF Dispersion 12>

200 g of a pulp (NBKP, manufactured by Nippon Paper Industries Co., Ltd.) on a dry mass basis and 24 g of sodium hydroxide on a dry mass basis were added to a pulper capable of stirring the pulp, and water was added so that a pulp solid concentration was 15%. Then, the mixture was stirred at 30° C. for 30 minutes, and then warmed to 70° C., 200 g (on an active matter basis) of 3-chloro-2-hydroxypropyltrimethylammonium chloride as a cationizing agent was added. After the reaction for 1 hour, the reaction mixture was separated, neutralized, and washed to give a cationically modified cellulose having a degree of substitution with cationic group of 0.05 per glucose unit. Then, the cationically modified pulp was adjusted to a solid concentration of 1%, and defibrated by 2 treatment cycles in a high pressure homogenizer at 20° C., 140 MPa to give a cellulose nanofiber dispersion (CNF dispersion 12). The resulting fibers had an average fiber diameter of 25 nm and an aspect ratio of 150. The CNF dispersion index of the CNF dispersion 12 was 0.

Example 16

The CNF dispersion 10 obtained above was dried in a drying oven at 105° C. to give a CNF dried solid having a water amount of 7%. The resulting CNF dried solid was pulverized by a dry mill to give additive cellulose nanofibers.

The above additive cellulose nanofibers were mixed in a commercially available lotion, and the mixture was stirred at 3000 rpm for 60 minutes to manufacture a cellulose nanofiber-containing lotion. The amount (bone dry mass) of the additive cellulose nanofibers added was 0.1% by mass based on 99.9% of the lotion. The resulting cellulose nanofiber-containing lotion was tested for stickiness and dripping.

<Dripping>

The lotion was sprayed on the skin, and visually evaluated based on the following criteria. The results are shown in Table 3.

A: A lotion remains on the skin without dripping off from the skin.
B: A lotion flows down from the skin after several minutes without dripping off from the skin for a while.
C: A lotion drips off from the skin, and flows down at once.

<Stickiness>

A lotion was sprayed on the skin of each of ten panelists, and the stickiness was evaluated according to the following 5-point method. The average score thereof was taken as the evaluation score. The results are shown in Table 3.

Score 5: Smooth without causing stickiness on the skin.
Score 3: Stickiness on the skin in some degree, but smooth.
Score 1: Stickiness on the skin, and uncomfortable.

Example 17

A cellulose nanofiber-containing lotion was manufactured and tested in the same manner as in Example 16 except that the CNF dispersion 10 of Example 16 was changed to the CNF dispersion 11.

Comparative Example 4

A lotion was manufactured and tested in the same manner as in Example 16 except that the additive cellulose nanofibers were not used.

Comparative Example 5

A lotion was manufactured and tested in the same manner as in Example 16 except that a carboxymethylated cellulose (trade name: F350HC-4, manufactured by Nippon Paper Industries Co., Ltd.) was used in place of the additive cellulose nanofibers.

TABLE 3

|  | Example 16 | Example 17 | Comparative Example 4 | Comparative Example 5 |
|---|---|---|---|---|
| Dripping | A | A | C | B |
| Stickiness | 3.8 | 4.2 | 2.2 | 2.0 |

As is apparent from the results in Table 3, it is found that Examples 16 and 17 containing cellulose nanofibers have better dripping and stickiness than those of Comparative Example 4 not containing cellulose nanofibers and Comparative Example 5 using a carboxymethylated cellulose.

Next, Examples of "rubber composition" will be shown. In the following Examples, the CNF dispersion index was measured in the same manner as in Example 1.

<Manufacture of CNF Dispersion 13>

To 500 mL of an aqueous solution of 780 mg of TEMPO (manufactured by Sigma Aldrich) and 75.5 g of sodium bromide dissolved therein was added 500 g (bone dry) of an unbeaten softwood bleached kraft pulp (brightness 85%), and the mixture was stirred until the pulp was homogeneously dispersed. An aqueous sodium hypochlorite solution was added to the reaction system in an amount of 6.0 mmol/g to start an oxidation reaction. During the reaction, the pH in the system decreased, and therefore, a 3M aqueous sodium hydroxide solution was sequentially added to adjust the reaction system to pH 10. The reaction was terminated when sodium hypochlorite has been consumed and the pH in the system became constant. After the reaction, the mixture was filtered through a glass filter to separate the pulp, and the pulp was thoroughly washed with water to give an oxidized pulp (carboxylated cellulose). The pulp yield was 90%, the time required for the oxidation reaction was 90 minutes, and the carboxy group content was 1.6 mmol/g.

The oxidized pulp obtained in the process described above was adjusted to 1.0% (w/v) with water, and treated in a ultra-high pressure homogenizer (20° C., 150 MPa) for three cycles to give a cellulose nanofiber dispersion (CNF dispersion 13). The resulting fibers had an average fiber diameter of 3 nm and an aspect ratio of 250. The CNF dispersion index of the CNF dispersion 13 was 0.

<Manufacture of CNF Dispersion 14>

In a stirrer capable of mixing pulp, 200 g of a pulp (NBKP (softwood bleached kraft pulp), manufactured by Nippon Paper Industries Co., Ltd.) on a dry mass basis and 111 g of sodium hydroxide on a dry mass basis were added and water was added in such an amount that the pulp had a solid content of 20% (w/v). Then, the mixture was stirred at 30° C. for 30 minutes, and then 216 g (on an active matter basis) of sodium monochloroacetate was added. The mixture was stirred for 30 minutes, and then warmed to 70° C. and stirred for 1 hour. Then, the reaction mixture was separated, neutralized, and washed to give a carboxymethylated pulp having a degree of substitution with carboxymethyl group of 0.25 per glucose unit. Then, the carboxymethylated pulp was adjusted to a solid content of 1% with water, and defibrated by 5 treatment cycles in a high pressure homogenizer at 20° C., 150 MPa to give a carboxymethylated cellulose fiber aqueous dispersion (CNF dispersion 14). The resulting fibers had an average fiber diameter of 15 nm and an aspect ratio of 150. The CNF dispersion index of the CNF dispersion 14 was 0.

<Manufacture of CNF Dispersion 15>

200 g of a pulp (NBKP, manufactured by Nippon Paper Industries Co., Ltd.) on a dry mass basis and 24 g of sodium hydroxide on a dry mass basis were added to a pulper capable of stirring the pulp, and water was added so that a pulp solid concentration was 15%. Then, the mixture was stirred at 30° C. for 30 minutes, and then warmed to 70° C., 200 g (on an active matter basis) of 3-chloro-2-hydroxypropyltrimethylammonium chloride as a cationizing agent was added. After the reaction for 1 hour, the reaction mixture was separated, neutralized, and washed to give a cationically modified cellulose having a degree of substitution with cationic group of 0.05 per glucose unit. Then, the cationically modified pulp was adjusted to a solid concentration of 1%, and defibrated by 2 treatment cycles in a high pressure homogenizer at 20° C., 140 MPa to give a cellulose nanofiber dispersion (CNF dispersion 15). The resulting fibers had an average fiber diameter of 25 nm and an aspect ratio of 150. The CNF dispersion index of the CNF dispersion 15 was 0.

Example 18

The CNF dispersion 13 obtained above was used as additive cellulose nanofibers. With the bone dry solid content of 100 g of rubber latex (trade name: HA Latex, REGITEX CO., LTD., solid content concentration: 65% by mass) was mixed 5% by mass of additive cellulose nanofibers in a bone dry amount, followed by stirring by using T.K. HOMO MIXER (8,000 rpm) for 60 minutes, to give a mixture. This mixture was dried in a heating oven at 70° C. for 10 hours to give a master batch.

With the master batch obtained by the above method, zinc oxide and stearic acid were mixed in amounts of 6% by mass and 0.5% by mass based on the rubber components in the master batch, respectively, and the mixture was kneaded by an open roll (manufactured by Kansai Roll Co., Ltd.) at 30° C. for 10 minutes to give a kneaded product. Sulfur and a vulcanization accelerator (BBS, N-t-butyl-2-benzothiazole sulfenamide) were added to the kneaded product in amounts of 3.5% by mass and 0.7% by mass, respectively, based on the rubber component in the kneaded product, and the mixture was kneaded by using an open roll (manufactured by Kansai Roll Co., Ltd.) at 30° C. for 10 minutes to give an unvulcanized rubber composition sheet. The resulting unvulcanized rubber composition sheet was sandwiched between molds and press-vulcanized at 150° C. for 10 minutes to give a vulcanized rubber sheet (vulcanized rubber composition) having a thickness of 2 mm. The resulting vulcanized rubber sheet was cut into test specimens having a predetermined shape, and the test specimens were measured for stresses during 100% strain and 300% strain, and breaking strength which exhibit tensile strength according to JIS K 6251 "Determination of Vulcanized Rubber and Thermoplastic Rubber-Tensile Properties". The larger the numerical value is, the better the reinforcement of the vulcanized rubber composition is, which exhibits excellent mechanical strength.

In the present example, the dispersion of the cellulose nanofibers in the rubber matrix was good, which provided excellent mechanical properties as shown in Table 4.

Example 19

A vulcanized rubber sheet was obtained in the same manner as in Example 18 except that the CNF dispersion 13 in Example 18 was changed to the CNF dispersion 14. The resulting vulcanized rubber sheet was evaluated.

Example 20

A vulcanized rubber sheet was obtained in the same manner as in Example 18 except that the CNF dispersion 13 in Example 18 was changed to the CNF dispersion 15. The resulting vulcanized rubber sheet was evaluated.

Comparative Example 6

A vulcanized rubber sheet was obtained in the same manner as in Example 18 except that the additive cellulose nanofibers were not used. The resulting vulcanized rubber sheet was evaluated.

Comparative Example 7

A vulcanized rubber sheet was obtained in the same manner as in Example 18 except that a carboxymethylated cellulose (trade name: F350HC-4, manufactured by Nippon Paper Industries Co., Ltd.) was used in place of the additive cellulose nanofibers. The resulting vulcanized rubber sheet was evaluated.

TABLE 4

|  | Example 18 | Example 19 | Example 20 | Comparative Example 6 | Comparative Example 7 |
| --- | --- | --- | --- | --- | --- |
| Stress during 100% strain (MPa) | 1.8 | 2.2 | 2.3 | 1.1 | 1.4 |
| Stress during 300% strain (MPa) | 5.9 | 6.4 | 6.5 | 2.6 | 3.9 |
| Stress at break (MPa) | 28.5 | 27.8 | 28.6 | 22.1 | 24.5 |

As is apparent from the results of Table 4, it is found that Examples 18, 19 and 20 containing cellulose nanofibers have better rubber physical properties than those of Comparative Example 6 not containing cellulose nanofibers and Comparative Example 7 using a carboxymethylated cellulose.

The invention claimed is:

1. A method for evaluating a cellulose nanofiber dispersion, the method comprising the steps of:
   (1) preparing a 1.0% by mass cellulose nanofiber aqueous dispersion;
   (2) adding a color material containing 5 to 20% by mass of a colored pigment having an average particle size of 0.03 μm or more and 1 μm or less to 1 g of the cellulose nanofiber aqueous dispersion prepared in the step (1), followed by stirring with a vortex mixer for 1 minute;
   (3) sandwiching the cellulose nanofiber aqueous dispersion containing the color material obtained in the step (2) between two glass plates so that a film thickness of the cellulose nanofiber aqueous dispersion is 0.15 mm;
   (4) observing a film of the cellulose nanofiber aqueous dispersion containing the color material sandwiched between the two glass plates obtained in the step (3) with a microscope (magnification: 100 times);
   (5) measuring major axes of aggregates existing in a range of 3 mm×2.3 mm in the step (4), and classifying the observed aggregates into an oversize aggregate having a major axis of 150 μm or more, a large size aggregate having a major axis of 100 μm or more and less than 150 μm, a middle size aggregate having a major axis of 50 μm or more and less than 100 μm, and a small size aggregate having a major axis of 20 μm or more and less than 50 μm; and (6) counting the number of the aggregates classified in the step (5), and calculating a CNF dispersion index according to the equation 1 to evaluate dispersibility of the cellulose nanofiber aqueous dispersion, the equation 1:

$$\text{CNF dispersion index} = (\text{the number of oversize aggregates} \times 512 + \text{the number of large size aggregates} \times 64 + \text{the number of middle size aggregates} \times 8 + \text{the number of small size aggregates} \times 1)=2.$$

2. A cellulose nanofiber aqueous dispersion having a CNF dispersion index of 8000 or less, the CNF dispersion index determined by the method according to claim 1.

3. A food comprising the cellulose nanofiber aqueous dispersion according to claim 2 or a cellulose nanofiber derived from the aqueous dispersion.

4. A dumpling comprising the cellulose nanofiber aqueous dispersion according to claim 2 or a cellulose nanofiber derived from the aqueous dispersion.

5. A water-containing chocolate comprising the cellulose nanofiber aqueous dispersion according to claim 2 or a cellulose nanofiber derived from the aqueous dispersion.

6. A cosmetic comprising the cellulose nanofiber aqueous dispersion according to claim 2 or a cellulose nanofiber derived from the aqueous dispersion.

7. A rubber composition comprising the cellulose nanofiber aqueous dispersion according to claim 2 or a cellulose nanofiber derived from the aqueous dispersion.

* * * * *